(12) United States Patent
Pavlyuk et al.

(10) Patent No.: US 8,575,069 B1
(45) Date of Patent: Nov. 5, 2013

(54) HUMAN PERFORMANCE BIOMARKER BINDING PEPTIDES FOR NEUROPEPTIDE Y AND METHODS OF USING THE SAME

(71) Applicant: The United States of America, as represented by the Secretary of the Air Force, Washington, DC (US)

(72) Inventors: Oksana M. Pavlyuk, Dayton, OH (US); Madhavi Kadakia, Dayton, OH (US); Joshua Hagen, Cincinnati, OH (US); Rajesh Naik, Dayton, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 13/741,637

(22) Filed: Jan. 15, 2013

(51) Int. Cl.
*C40B 30/04* (2006.01)
(52) U.S. Cl.
USPC .................................................. 506/9; 506/7
(58) Field of Classification Search
USPC ........................................................ 506/7, 9
See application file for complete search history.

(56) References Cited

U.S. PATENT DOCUMENTS

2005/0147964 A1 * 7/2005 Yamakawa et al. ............... 435/5

OTHER PUBLICATIONS

Grouzmann et al, Clinical Chemistry, 2001; 47:6, 1075-1082.*
Gao et al, Phys. Chem. Chem. Phys., 2012, 14, 9460-9467.*
Čípková, Jiřina, "Autofagie a charakterizace epitopŮ anti-ATG4A protilátek pomocí „phage display", Bakalářská práce, Masarykova Univerzita, original Czechoslovakian language version, published online May 2012, machine translated version of website available at <http://translate.google.com/translate?hl=en&sl=cs&u=http://is.muni.cz/th/357691/prif_b/&prev=/search%3Fq%3D%2522%-25C4%258C%25C3%25ADpkov%25C3%25A1,%2BJi%25C5%-2599ina%2522%26biw%3D1680%26bih%3D834>.
Čáipková, Jiřina, "Autophagy and Characterization of Anti-epitope Antibodies by ATG4A "Phage Display"," Bachelor Thesis, Masarykova University, machine-generated English language translation, published online May 2012.
Zhang, Lei, et al., "The neuropeptide Y system: Pathophysiological and therapeutic implications in obesity and cancer," Pharmacology & Therapeutics 131 (2011) pp. 91-113.
Gehlert, D.R., "Introduction to the reviews on neuropeptide Y," Neuropeptides 38 (2004) pp. 135-140.
Mendonsa, Shaun D., et al., "In Vitro Selection of Aptamers with Affinity for Neuropeptide Y Using Capillary Electrophoresis," J. Am. Chem. Soc. 2005, 127, pp. 9382-9383.

* cited by examiner

*Primary Examiner* — Christopher M Babic
*Assistant Examiner* — Valerie Toodle
(74) *Attorney, Agent, or Firm* — AFMCLO/JAZ; Rebecca Greendyke

(57) ABSTRACT

Peptides against neuropeptide Y (NPY), a biomarker associated with human performance and cognition, and methods of using the peptides to detect NPY.

7 Claims, 4 Drawing Sheets

HUMAN PERFORMANCE BIOMARKER BINDING PEPTIDES FOR NEUROPEPTIDE Y AND METHODS OF USING THE SAME

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates generally to the field of biomarker detection. More particularly, it relates to peptides against neuropeptide Y and methods of using the same.

2. Description of the Related Art

Biomarkers are present in a variety of easily-accessible bodily fluids, including saliva, sweat, blood, and urine, and may be used to predict, identify, and monitor medical disorders and diseases ranging from mental disorders such as schizophrenia to cancer and bacterial and viral infections. Neuropeptide Y (NPY) is a highly abundant and structurally conserved neurotransmitter that has been implicated in a number of important physiological functions, including energy homeostasis, stress response, and anxiolysis. In addition to the therapeutic potential of NPY-related drugs in treatment of hypertension, obesity, and depression, there is also evidence that NPY is an important biomarker of neurological health. Therefore, detection and monitoring of NPY levels is of the utmost importance in identifying and diagnosing brain trauma, as well as stress- and anxiety-related disorders, including post-traumatic stress disorder (PTSD).

Many traditional methods for detection of NPY and other biomarkers rely on complex, time consuming, and expensive assays using antibodies. Antibodies raised in various species against NPY often exhibit cross-reactivity when used as sensing elements in microarrays, and the production process is laborious and cost-ineffective. Moreover, antibodies are large, multi-domain proteins with a short shelf-life as a result of protein denaturation, which limits their scope in biosensor development. Other detection methods such as radioimmunoassay (RIA) or enzyme linked immunosorbent assay (ELISA) require trained technicians, specialized equipment, and long analysis times. Therefore, development of alternative detection methods is required for efficient physiological monitoring of NPY levels.

Previously, short oligonucleotide sequences referred to as aptamers have been isolated against NPY and other biomarkers. However, the aptamer selection process suffers from considerable disadvantages. Selection of NPY-binding oligonucleotides is performed in free solution, and aptamers bound to the target NPY are subsequently separated from non-binding oligonucleotides by capillary electrophoresis. In order to achieve effective separation, the injection volume, i.e. the pool of random nucleic acid sequences is rather low. It is important to use as many different sequences as possible in the first selection round to increase the number of potential specific NPY binders, and low injection volume significantly limits the effectiveness of selection. Moreover, negatively charged nucleic acids require counter cations and special buffer systems to be able to fold correctly into their active state, and these requirements generally limit their ability to bind to NPY (pI=5.5).

SUMMARY OF THE INVENTION

The present invention includes a composition comprising at least one peptide sequence for detecting neuropeptide Y, the peptide sequence being selected from the group consisting of SEQ ID NOs:1-3.

The present invention further includes a method for detecting neuropeptide Y comprising the steps of: immobilizing one or more peptides onto a surface; preparing a sample obtained from a patient; contacting the sample with the peptides; and detecting binding of neuropeptide Y to the peptides.

In one embodiment of the method, the peptide comprises at least one of SEQ ID NOs:1-3. In another embodiment, each peptide has a pI of between 8.0-10.0.

In one embodiment of the method, the detecting step comprises use of a carbon nanotube field effect transistor. The carbon nanotubes are functionalized with one or more peptides, and binding of NPY to the peptides causes a change in the carbon nanotubes' electrical conductivity.

In an alternative embodiment, the detecting step comprises use of a gold nanoparticle-based colorimetric assay. Gold particles are functionalized with one or more peptides, and binding of NPY to the peptides causes a colorimetric shift.

In a further embodiment, the detecting step comprises use of a protein microarray. Peptides are immobilized on a solid surface, and binding of NPY to the peptides is detected by probing with one or more antibodies.

In another embodiment, the method further comprises determining, based on detection of neuropeptide Y in the sample, whether the patient is suffering from at least one of an anxiety-related disorder and a traumatic brain injury.

DETAILED DESCRIPTION OF THE INVENTION

Figure 1:
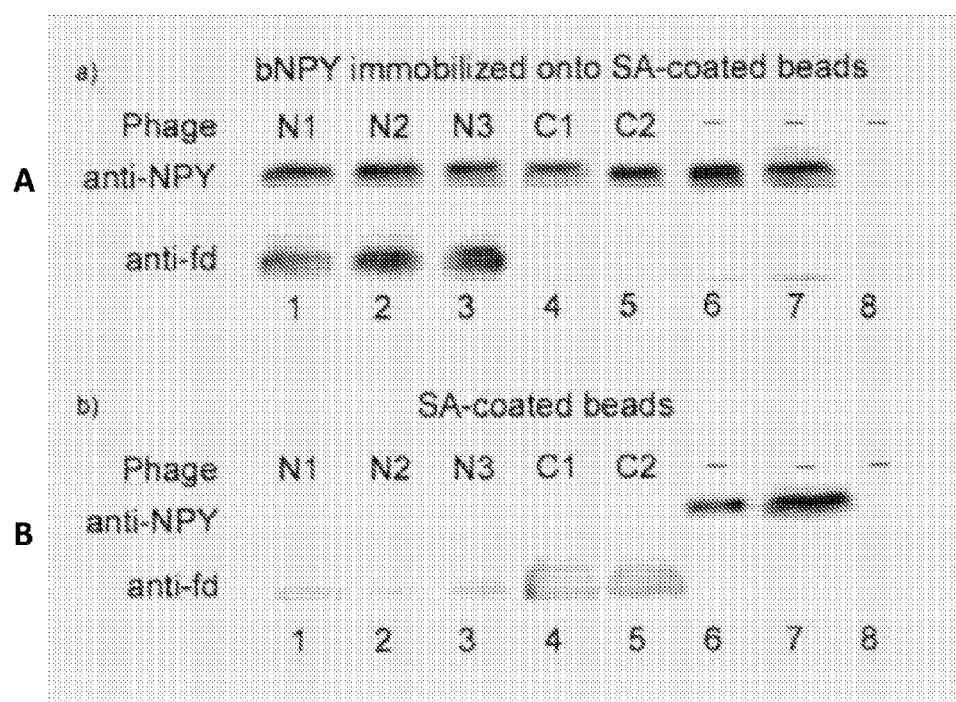
FIG. 1 is a Western blot illustrating the binding affinity of SEQ ID NOs 1-5 to their respective targets.

The present invention includes binding peptides against neuropeptide Y (NPY), a biomarker associated with human performance and cognition. NPY is present in a variety of fluids such as saliva, sweat, blood, and urine and may be used in the development of sensors for a wide array of applications, such as clinical diagnostics and human performance monitoring. The invention further includes methods of using the binding peptides to detect NPY.

Several short amino acid sequences with high selectivity, binding affinity, and specificity for NPY have been identified. These short sequences are only 12 amino acids in length, giving them several advantages over larger, existing molecular recognition elements. In contrast to oligonucleotide aptamers, the 12-mer peptides isolated with phage display rely on protein-protein interactions, which more closely resemble in vivo binding interactions with the respective receptors. Additionally, the small size of the dodecameric peptides makes them ideal candidates for applications in biosensor development. For example, in the case of microarray-based sensors, more peptides per unit area may be immobilized onto a solid support, thus increasing the target limit of detection. Additionally, synthesis of the peptides and their analogues is inexpensive, and they are amenable to functionalization with nanomaterials. As compared to antibodies, small peptides are considerably more stable, resulting in potentially reusable biosensors with a longer biosensor shelf life.

NPY is a biomarker associated with several physiological states, with stress, cognition, and brain injury being just a few. A series of dodecamer peptides were identified from a combinatorial library as specific binders to NPY. Selectivity of the isolated peptides for NPY was confirmed with immunoblotting, while binding affinity was determined with surface plasmon resonance and quartz crystal microbalance assays. These newly isolated NPY-binding peptides may serve as templates for the construction of synthetic analogues and their variants, giving rise to a number of analyte-specific reagents exhibiting high affinity, selectivity, and specificity for NPY.

These highly specific NPY-binding peptides may further be used to detect NPY in biological samples in order to identify traumatic brain injury and monitor human performance. Detection and monitoring of NPY is particularly important for persons performing tasks requiring a large amount of cognition and concentration, as well as military and civilian patients undergoing treatment for a variety of conditions, including post-traumatic stress disorder (PTSD) and traumatic brain injury (TBI) treatment and other physiological states. The peptides may further be incorporated into highly sensitive biosensors for the detection of NPY and for monitoring of human performance and cognition.

Isolation of the binding peptide sequences was accomplished by an in vitro screening process referred to as phage display, the underlying principle of which relies on the expression of short peptides as fusions to bacteriophage coat proteins and their display on the surface of viral particles, providing a link between the displayed peptide and the viral DNA encoding it. Through an affinity selection process known as biopanning, phages displaying peptides with high affinity for the target molecule are separated from non-binding peptides, followed by elution and amplification. The ssDNA of the binding peptides is then sequenced to determine the peptide sequence.

The following examples and methods are presented as illustrative of the present invention or methods of carrying out the invention, and are not restrictive or limiting of the scope of the invention in any manner. The amino acid sequences are according to the standard three-letter or one-letter amino acid code as set out in Table 1. Referring to the drawings, like reference numerals may designate like or corresponding parts throughout the several views.

Example 1

Selection of NPY-Binding Peptides

50 µl of streptavidin-coated magnetic beads are saturated with biotinylated NPY (bNPY), followed by confirmation of NPY immobilization by immunoblotting. The exact amount of bNPY required to saturate a given quantity of streptavidin-coated beads is determined by performing a series of SDS-PAGE experiments with increasing bNPY concentrations. It is found that the theoretical binding capacity of a hypothetical biotinylated peptide is exceeded two-fold by the actual binding capacity of bNPY to the streptavidin-coated magnetic beads.

Four rounds of affinity selection are performed using both the immobilized bNPY and the streptavidin-coated magnetic beads as targets according to the biopanning procedure adapted from the Ph.D.™-12 Phage Display Peptide Library kit (New England BioLabs) protocol. After the first round of biopanning, no peptides with consensus sequences were isolated from a 12-mer peptide library, which is likely due to the fact that peptides exhibiting favorable growth properties and those binding non-specifically to the bNPY are isolated along with the peptides with preferential affinity for bNPY. For this reason, a negative selection step is introduced in the second round of biopanning, where the input phage is "pre-cleared" with streptavidin-coated beads to remove the non-specific binders.

After the second round of selection, a consensus sequence emerges and persists in the third and fourth rounds (Table 2, SEQ ID NO:2; N2). Two additional consensus sequences are isolated after the third and fourth rounds (Table 2, SEQ ID NO:1, 3; N1, N3). However, the three different peptide sequences do not share similar amino acid motifs; rather, all three share a similar isoelectric point (pI) of around 8.5-9.9. In addition, when streptavidin-coated beads are used as a target, sequences with an HPQ motif characteristic of the peptides binding to streptavidin are isolated after the third and fourth rounds of panning (Table 2, C1 and C2).

TABLE 1

| Amino Acid Code | | |
|---|---|---|
| Alanine | Ala | A |
| Cysteine | Cys | C |
| Aspartic Acid | Asp | D |
| Glutamic Acid | Glu | E |
| Phenylalanine | Phe | F |
| Glycine | Gly | G |
| Histidine | His | H |
| Isoleucine | Ile | I |
| Lysine | Lys | L |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

TABLE 2

| Binding Peptides | | | | |
|---|---|---|---|---|
| Seq ID NO | Peptide | Sequence | MW (g/mol) | pI |
| 1 | N1 | VQHNTKYSVVIR | 1443.67 | 9.99 |
| 2 | N2 | YHPNGMNPYTKA | 1392.55 | 8.50 |
| 3 | N3 | FPNWSLRPMNQM | 1520.79 | 9.75 |
| 4 | C1 | LTTQTLWDNHPQ | 1453.57 | 5.08 |
| 5 | C2 | HGIDGLQMWHPQ | 1418.59 | 5.97 |

Example 2

Affinity Confirmation of NPY-Binding Peptides

Specificity of the interactions between NPY and the NPY-binding peptides selected from phage display as described in Example 1 is determined by SDS-PAGE and subsequent immunoblotting, which is shown in FIG. 1. bNPY is immobilized onto streptavidin-coated magnetic beads, which are subsequently incubated with phages containing either NPY-binding peptide or the streptavidin-binding peptide with an HPQ motif. Streptavidin-coated magnetic beads alone are also incubated with bacteriophages displaying the corresponding fusion peptides. Excess unbound phage is washed away, the peptides are separated by SDS-PAGE, and binding is analyzed using either rabbit α-fd or α-NPY as a primary Ab and goat α-rabbit HRP conjugate as a secondary Ab.

The Western blot in FIG. 1A (labeled "bNPY immobilized onto SA-coated beads") contains the streptavidin-coated beads with bNPY, and FIG. 1B (labeled "SA-coated beads") contains the streptavidin-coated beads alone. In both FIGS. 1A and 1B, lanes 1-3 contain SEQ ID NOs:1-3 (N1-N3), and lanes 4-5 contain SEQ ID NOs:4-5 (C1 and C2), each at a concentration of approximately $1\times10^{10}$ pfu/mL. The upper row in each of FIGS. 1A and 1B is probed with rabbit α-NPY, while the lower row is rabbit α-fd. As controls, lane 6 contains 4 μg bNPY/25 μl magnetic beads, lane 7 contains 2 μg bNPY, and lane 8 contains 2 μg streptavidin.

As shown in lanes 1-3 in FIG. 1A, strong binding is observed between bNPY and the phage displaying the bNPY-binding peptides. Strong binding is also detected between the streptavidin-coated magnetic beads and the phage displaying the peptide with an HPQ motif as seen in lanes 4-5 of FIG. 1B. A small amount of binding is observed between the phages with NPY-binding sequences and the streptavidin-coated beads (FIG. 1B, lanes 1-3), which is potentially due to non-specific interactions between the multi-domain streptavidin protein and the bacteriophage coat proteins.

Figure 2:
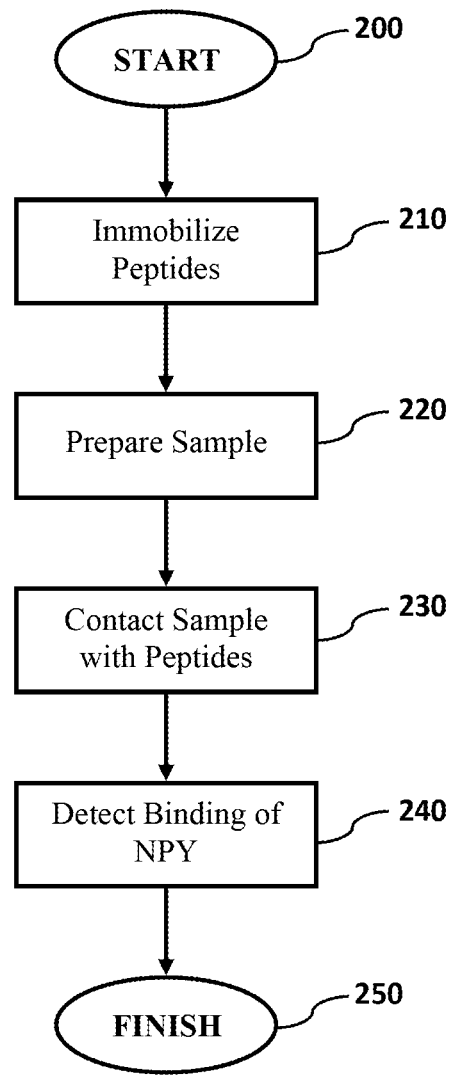
FIG. 2 is a flowchart depicting an exemplary embodiment of a method of using peptides to detect NPY in a sample according to the present invention.

The present invention further includes methods of using the peptides to detect NPY in a sample. FIG. 2 is a flowchart depicting an exemplary embodiment of the method. The method begins (Step 200) with immobilization of one or more NPY-binding peptides according to the present invention (Step 210) onto a surface. A sample obtained from a patient is prepared for testing according to known methods that are appropriate for the sample type (Step 220). The sample may be a biological sample including, but not limited to, saliva, sweat, urine, and blood or a blood component or fraction such as serum or plasma. Preparation of the sample may include one or more processing steps such as concentration or dilution of the sample, as well as separation of sample components or fractions.

The prepared sample is then contacted with the immobilized peptides (Step 230). NPY in the sample is identified by detecting binding of the NPY to the peptides (Step 240), and the method terminates (Step 250). Detection of NPY binding to the peptides is generally via a positive or negative result, and in some embodiments, the result may be visualized by the naked eye or with a UV-vis spectrometer. In one embodiment of the method, based on the presence of NPY in the sample, it may be determined that the patient is experiencing high levels of stress and/or is suffering from a TBI or an anxiety-related disorder such as PTSD.

In one embodiment of the method, the peptides comprise one or more of SEQ ID NOs:1-3 (Table 1, N1-N3). In another embodiment, the peptides each comprise a pI of between 8.0 and 10.0 In a further embodiment, the peptides each comprise a pI of between 8.5 and 10.0.

Figure 3:
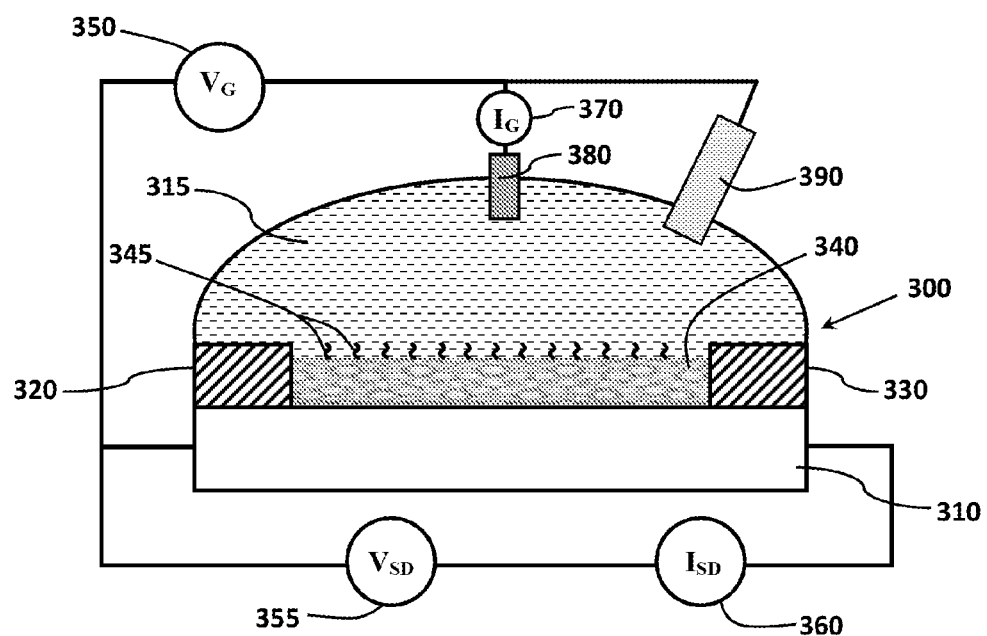
FIG. 3 is a side view of an exemplary embodiment of a carbon nanotube field effect transistor.

In one embodiment of the method, the peptides may be used to functionalize carbon nanotubes (CNT), which may be used as a component of a CNT field effect transistor (FET). Binding of NPY to the peptides alters a material property of the CNTs, such as electrical conductivity, which may be harnessed to create a biosensor. FIG. 3 is a side view of an exemplary embodiment of a CNT-FET biosensor 300 according to the present invention. The CNT-FET biosensor 300 depicted in FIG. 3 is a liquid-gate FET configuration for use in an aqueous environment. The CNT-FET biosensor 300 comprises a substrate 310, which may comprise any commercially available thermally stable conducting material such as doped silicon or silicon oxide. The CNT-FET biosensor 300 further comprises a source electrode 320 and a drain electrode 330 that sit atop the substrate 310. The source electrode 320 and drain electrode 330 may each comprise chromium, gold, silver, copper, and/or other suitable conductive materials or alloys thereof.

The source electrode 320 and drain electrode 330 form a channel, which contains CNTs 340 in a monolayer network. The CNTs 340 may be deposited on the substrate 310 using carbon vapor deposition or other suitable known methods, followed by immobilization of NPY-binding peptides 345 according to the present invention onto the surface of the CNTs 340. Depending on the density of the CNTs 340, the completed CNT-FET biosensor 300 may have a channel width of about 2-100 micrometers. After deposition of the CNTs 340, conventional microlithography may be used to pattern a metal layer on top of the CNTs 340 to create the source electrode 320 and drain electrode 330.

Alternatively, the CNT-FET biosensor 300 may be fabricated by depositing the CNTs 340 onto a pre-assembled FET device using a dielectrophoresis field or other suitable method of deposition such as spray-painting and drop-casting. Commercially obtained CNTs 340 may be functionalized with the peptides 345 prior to deposition on the substrate 310. Alternatively, the CNTs 340 may be deposited onto the pre-assembled FET device, followed by functionalization of the CNTs 340 with the peptides 345.

In FIG. 3, an aqueous buffer solution 315 surrounds the channel containing the CNTs 340 and serves as the liquid gate. A gate electrode 380 serves as the voltage control to the liquid gate. The gate electrode 380 may comprise platinum or other suitable conductive material. The reference 390 monitors an applied electrochemical potential. A gate-source voltage ($V_G$) 350 is applied to the gate electrode 380, which induces a gate current ($I_G$) 370 that is monitored to ensure the sensing signal is not from the electrochemical side reactions. A second bias voltage ($V_{SD}$) 355 is created between the source electrode 320 and the drain electrode 330. Electrons flow from the source electrode 320 to the drain electrode 330 via the CNTs 340, creating a source-drain current ($I_{SD}$) 360. The $I_{SD}$ 360 may be modulated by altering the $V_G$ 350. Binding of NPY in the sample to the peptides 345 on the surface of the CNTs 340 causes a change in the $I_{SD}$ 360, which may be monitored and detected to identify the presence of NPY in the sample.

In another embodiment of the method, the peptides may be used to functionalize gold nanoparticles for use in a gold nanoparticle-based colorimetric assay. Gold nanoparticles have distinctive optical features that make them ideal for use in colorimetric assays of molecular interactions, and gold nanoparticles functionalized with peptide or nucleic acid sequences have been used to detect a variety of targets including proteins, nucleic acids, carbohydrates, and metal ions. Binding with a target molecule causes a colorimetric shift based on nanoparticle aggregation and/or changes to interparticle distances. The shift may be a visible light shift, such as changing from red to blue, which may be monitored by the naked eye or by a UV-vis spectrometer. The interaction between the functionalized gold nanoparticles and the target may be visualized in solution, such as by spotting onto a microtiter plate or a thin layer chromatography plate. The interaction may alternatively be visualized via separation using an appropriate gel electrophoresis method. The various bound and unbound components are separated by size, and the bands may also reflect the color shift.

Figure 4:
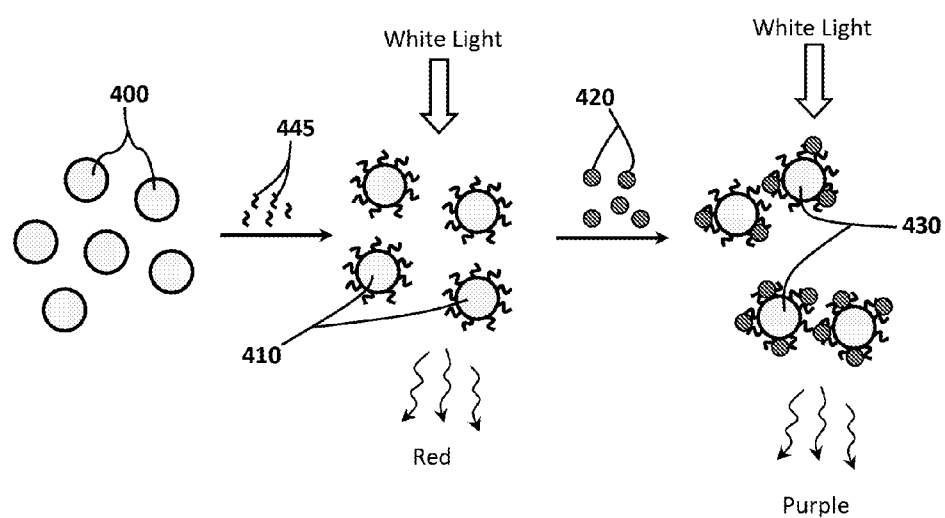
FIG. 4 is an exemplary embodiment of a method of colorimetric detection of NPY using gold nanoparticles.

FIG. 4 is an exemplary embodiment of colorimetric detection of NPY using a gold nanoparticle-based colorimetric assay. Peptides 445 according to the present invention are immobilized onto the outer surface of gold nanoparticles 400 to form functionalized gold nanoparticles 410. A sample containing NPY 420 is introduced, and the NPY 420 binds to the peptides 445 on the functionalized gold nanoparticles 410 to form nanoparticle-NPY complexes 430. This binding may be visualized by a colorimetric shift. For example, when illuminated with white light, the functionalized gold nanoparticles 410 appear one color, which is shown as "Red" in the example in FIG. 4. Binding of the NPY 420 causes a color shift in the nanoparticle-NPY complexes 430, in this case to "Purple," which may be visualized and used to detect the presence of NPY 420.

In a further embodiment of the method, the peptides may be used as part of an immunoassay, including, but not limited to, protein microarrays. In one embodiment, peptides according the present invention are immobilized directly onto a solid surface such as a glass slide or microtiter plate. A prepared sample suspected of containing NPY is contacted with the peptides, and binding of NPY to the peptides is detected via probing with α-NPY antibody (primary antibody) according to known methods (reverse phase array or RPA). The α-NPY antibody may further comprise an enzyme conjugate such as horseradish peroxidase that elicits a detectable change upon addition of an appropriate enzyme substrate. This detectable change may include a change in color that is visible to the naked eye or to a UV-vis spectrometer or a change in fluorescence. The method may alternatively include use of a secondary antibody according to known methods, and this secondary antibody may further comprise an enzyme conjugate.

Although this invention has been described with respect to certain preferred embodiments, various other embodiments and various changes and modifications to the disclosed embodiment(s) will become apparent to those skilled in the art. All such other embodiments, changes, and modifications are intended to come within the spirit and scope of the appended claims.

What is claimed is:

1. An isolated peptide for detecting neuropeptide Y identified from a combinatorial library, the isolated peptide being selected from the group consisting of SEQ ID NOs:1-3.

2. A method for detecting neuropeptide Y comprising the steps of: providing at least one peptide selected from the group consisting of SEQ ID NOs: 1-3; contacting the at least one peptide selected from the group consisting of SEQ ID NOs: 1-3 with a prepared sample; and, detecting binding of neuropeptide Y in the prepared sample to the at least one peptide selected from the group consisting of SEQ ID NOs: 1-3.

3. The method of claim 2 wherein each peptide has a pI of between about 8.0 and 10.0.

4. The method of claim 2 wherein the detecting step comprises use of a carbon nanotube field effect transistor.

5. The method of claim 2 wherein the detecting step comprises use of a gold nanoparticle-based colorimetric assay.

6. The method of claim 2 wherein the detecting step comprises use of a protein microarray.

7. A composition consisting essentially of a plurality of isolated peptides according to claim 1.

* * * * *

SEQUENCE LISTING

<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: Generated by phage peptide display

<400> SEQUENCE: 1

Val Gln His Asn Thr Lys Tyr Ser Val Val Ile Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Generated by phage peptide display

<400> SEQUENCE: 2

Tyr His Pro Asn Gly Met Asn Pro Tyr Thr Lys Ala
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Generated by phage peptide display

<400> SEQUENCE: 3

Phe Pro Asn Trp Ser Leu Arg Pro Met Asn Gln Met
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Generated by phage peptide display

<400> SEQUENCE: 4

-continued

```
Leu Thr Thr Gln Thr Leu Trp Asp Asn His Pro Gln
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Generated by phage peptide display

<400> SEQUENCE: 5

His Gly Ile Asp Gly Leu Gln Met Trp His Pro Gln
1               5                   10
```